(12) United States Patent
Binmoeller

(10) Patent No.: US 8,784,437 B2
(45) Date of Patent: *Jul. 22, 2014

(54) METHODS AND DEVICES FOR ENDOSONOGRAPHY-GUIDED FUNDOPLEXY

(75) Inventor: Kenneth F. Binmoeller, Rancho Santa Fe, CA (US)

(73) Assignee: Xlumena, Inc., Mountain View, CA (US)

( * ) Notice: Subject to any disclaimer, the term of this patent is extended or adjusted under 35 U.S.C. 154(b) by 590 days.

This patent is subject to a terminal disclaimer.

(21) Appl. No.: 11/449,365

(22) Filed: Jun. 8, 2006

(65) Prior Publication Data

US 2006/0282087 A1 Dec. 14, 2006

Related U.S. Application Data

(60) Provisional application No. 60/688,837, filed on Jun. 9, 2005.

(51) Int. Cl.
*A61B 17/04* (2006.01)

(52) U.S. Cl.
USPC ............ 606/144; 606/148; 606/228; 606/223

(58) Field of Classification Search
USPC ......... 606/153, 220, 144, 139, 145–148, 228, 606/232
See application file for complete search history.

(56) References Cited

U.S. PATENT DOCUMENTS

| | | |
|---|---|---|
| 2,127,903 A | 8/1938 | Bowen |
| 3,039,468 A | 6/1962 | Price |
| 3,717,151 A | 2/1973 | Collett |
| 3,874,388 A | 4/1975 | King et al. |
| 3,970,090 A | 7/1976 | Loiacono |
| 4,173,392 A | 11/1979 | Ekinaka et al. |
| 4,235,238 A | 11/1980 | Ogiu et al. |
| 4,587,972 A | 5/1986 | Morantte, Jr. |
| 4,608,965 A | 9/1986 | Anspach, Jr. et al. |
| 4,705,040 A | 11/1987 | Mueller et al. |

(Continued)

FOREIGN PATENT DOCUMENTS

| | | |
|---|---|---|
| EP | 637431 A1 | 2/1995 |
| EP | 1314404 A2 | 5/2003 |

(Continued)

OTHER PUBLICATIONS

Fritscher-Ravens, Annette, M.D., et al., A Through-the-Scope Device for Suturing and Tissue Approximation Under EUS Control; Gastro Endo; (2002) 56:5, pp. 737-742.

(Continued)

*Primary Examiner* — Corrine M McDermott
*Assistant Examiner* — Alexander Orkin
(74) *Attorney, Agent, or Firm* — Shay Glenn LLP

(57) ABSTRACT

The present invention relates to a tissue securement system, device and method for endoscopy or endosonography-guided transluminal interventions whereby a ligation or anchor is placed and secured into soft tissue. An objective of this invention is to provide a method to reduce gastroesophageal reflux by endosonography-guided intervention. Specifically, endosonography is used to insert a ligation element through the esophageal wall, through the diaphragmatic crus and into the fundus of the stomach. This ligation element placed from the esophagus and around the Angle of His to create a barrier to gastroesophageal reflux.

13 Claims, 6 Drawing Sheets

(56) References Cited

U.S. PATENT DOCUMENTS

| | | | |
|---|---|---|---|
| 4,790,813 A | 12/1988 | Kensey | |
| 4,869,263 A | 9/1989 | Segal et al. | |
| 4,896,678 A | 1/1990 | Ogawa | |
| 4,917,097 A | 4/1990 | Proudian et al. | |
| 4,920,967 A | 5/1990 | Cottonaro et al. | |
| 4,950,285 A * | 8/1990 | Wilk | 606/232 |
| 4,973,317 A | 11/1990 | Bobrove | |
| 4,990,139 A | 2/1991 | Jang | |
| 5,024,655 A | 6/1991 | Freeman et al. | |
| 5,064,435 A | 11/1991 | Porter | |
| 5,180,392 A | 1/1993 | Skeie et al. | |
| 5,183,464 A | 2/1993 | Dubrul | |
| 5,197,971 A | 3/1993 | Bonutti | |
| 5,207,229 A | 5/1993 | Winters | |
| 5,209,727 A | 5/1993 | Radisch, Jr. et al. | |
| 5,211,651 A | 5/1993 | Reger et al. | |
| 5,221,258 A | 6/1993 | Shturman | |
| 5,224,945 A | 7/1993 | Pannek, Jr. | |
| 5,226,421 A | 7/1993 | Frisbie et al. | |
| 5,234,447 A | 8/1993 | Kaster et al. | |
| 5,246,007 A | 9/1993 | Frisbie et al. | |
| 5,257,990 A | 11/1993 | Nash | |
| 5,258,000 A | 11/1993 | Gianturco | |
| 5,261,920 A | 11/1993 | Main et al. | |
| 5,275,610 A | 1/1994 | Eberbach | |
| 5,275,611 A | 1/1994 | Behl | |
| 5,290,249 A | 3/1994 | Foster et al. | |
| 5,304,198 A | 4/1994 | Samson | |
| 5,330,497 A | 7/1994 | Freitas et al. | |
| 5,353,785 A | 10/1994 | Wilk | |
| 5,368,595 A * | 11/1994 | Lewis | 606/151 |
| 5,372,588 A | 12/1994 | Farley et al. | |
| 5,381,788 A | 1/1995 | Matula et al. | |
| 5,395,349 A | 3/1995 | Quiachon et al. | |
| 5,443,484 A | 8/1995 | Kirsch et al. | |
| 5,458,131 A | 10/1995 | Wilk | |
| 5,462,561 A | 10/1995 | Voda | |
| 5,470,337 A | 11/1995 | Moss | |
| 5,495,851 A | 3/1996 | Dill et al. | |
| 5,520,700 A | 5/1996 | Beyar et al. | |
| 5,531,699 A | 7/1996 | Tomba et al. | |
| 5,536,248 A | 7/1996 | Weaver et al. | |
| 5,588,432 A | 12/1996 | Crowley | |
| 5,601,588 A | 2/1997 | Tonomura et al. | |
| 5,603,698 A | 2/1997 | Roberts et al. | |
| 5,620,456 A | 4/1997 | Sauer et al. | |
| 5,620,457 A | 4/1997 | Pinchasik et al. | |
| 5,662,664 A | 9/1997 | Gordon et al. | |
| 5,688,247 A | 11/1997 | Haindl et al. | |
| 5,697,944 A | 12/1997 | Lary | |
| 5,709,671 A | 1/1998 | Stephens et al. | |
| 5,709,707 A | 1/1998 | Lock et al. | |
| 5,713,870 A | 2/1998 | Yoon | |
| 5,725,552 A | 3/1998 | Kotula et al. | |
| 5,797,906 A | 8/1998 | Rhum et al. | |
| 5,817,062 A | 10/1998 | Flom et al. | |
| 5,827,276 A | 10/1998 | LeVeen et al. | |
| 5,843,116 A | 12/1998 | Crocker et al. | |
| 5,843,127 A | 12/1998 | Li | |
| 5,853,421 A | 12/1998 | Leschinsky et al. | |
| 5,853,422 A | 12/1998 | Huebsch et al. | |
| 5,855,576 A | 1/1999 | LeVeen et al. | |
| 5,857,999 A | 1/1999 | Quick et al. | |
| 5,858,006 A | 1/1999 | Van der Aa et al. | |
| 5,882,340 A | 3/1999 | Yoon | |
| 5,893,856 A | 4/1999 | Jacob et al. | |
| 5,897,567 A | 4/1999 | Ressemann et al. | |
| 5,935,107 A | 8/1999 | Taylor et al. | |
| 5,944,738 A | 8/1999 | Amplatz et al. | |
| 5,951,576 A | 9/1999 | Wakabayashi | |
| 5,951,588 A | 9/1999 | Moenning | |
| 5,957,363 A | 9/1999 | Heck | |
| 5,993,447 A | 11/1999 | Blewett et al. | |
| 6,007,522 A | 12/1999 | Agro et al. | |
| 6,007,544 A | 12/1999 | Kim | |
| 6,017,352 A | 1/2000 | Nash et al. | |
| 6,022,359 A | 2/2000 | Frantzen | |
| 6,036,698 A | 3/2000 | Fawzi et al. | |
| 6,074,416 A | 6/2000 | Berg et al. | |
| 6,080,174 A | 6/2000 | Dubrul et al. | |
| 6,113,609 A | 9/2000 | Adams | |
| 6,113,611 A | 9/2000 | Allen et al. | |
| 6,190,353 B1 | 2/2001 | Makower et al. | |
| 6,228,039 B1 | 5/2001 | Binmoeller | |
| 6,231,515 B1 | 5/2001 | Moore et al. | |
| 6,231,587 B1 | 5/2001 | Makower | |
| 6,241,758 B1 | 6/2001 | Cox | |
| 6,251,084 B1 | 6/2001 | Coelho | |
| 6,264,675 B1 * | 7/2001 | Brotz | 606/228 |
| 6,290,485 B1 | 9/2001 | Wang | |
| 6,309,415 B1 | 10/2001 | Pulnev et al. | |
| 6,322,495 B1 | 11/2001 | Snow et al. | |
| 6,334,446 B1 | 1/2002 | Beyar | |
| 6,348,064 B1 | 2/2002 | Kanner | |
| 6,358,264 B2 | 3/2002 | Banko | |
| 6,371,964 B1 | 4/2002 | Vargas et al. | |
| 6,371,965 B2 | 4/2002 | Gifford et al. | |
| 6,391,036 B1 | 5/2002 | Berg et al. | |
| 6,402,770 B1 | 6/2002 | Jessen | |
| 6,432,040 B1 * | 8/2002 | Meah | 600/37 |
| 6,436,119 B1 | 8/2002 | Erb et al. | |
| 6,447,524 B1 | 9/2002 | Knodel et al. | |
| 6,447,533 B1 | 9/2002 | Adams | |
| 6,454,765 B1 | 9/2002 | LeVeen et al. | |
| 6,475,168 B1 | 11/2002 | Pugsley, Jr. et al. | |
| 6,475,185 B1 | 11/2002 | Rauker et al. | |
| 6,475,222 B1 | 11/2002 | Berg et al. | |
| 6,485,496 B1 | 11/2002 | Suyker et al. | |
| 6,488,653 B1 | 12/2002 | Lombardo | |
| 6,508,252 B1 | 1/2003 | Berg et al. | |
| 6,520,908 B1 | 2/2003 | Ikeda et al. | |
| 6,535,764 B2 | 3/2003 | Imran et al. | |
| 6,547,776 B1 | 4/2003 | Gaiser et al. | |
| 6,575,967 B1 | 6/2003 | LeVeen et al. | |
| 6,610,100 B2 | 8/2003 | Phelps et al. | |
| 6,614,595 B2 | 9/2003 | Igarashi | |
| 6,616,675 B1 | 9/2003 | Evard et al. | |
| 6,620,122 B2 | 9/2003 | Stinson et al. | |
| 6,626,917 B1 | 9/2003 | Craig | |
| 6,626,919 B1 | 9/2003 | Swanstrom | |
| 6,632,197 B2 | 10/2003 | Lyon | |
| 6,635,068 B1 | 10/2003 | Dubrul et al. | |
| 6,638,213 B2 | 10/2003 | Ogura et al. | |
| 6,645,205 B2 | 11/2003 | Ginn | |
| 6,656,182 B1 * | 12/2003 | Hayhurst | 606/232 |
| 6,656,206 B2 | 12/2003 | Corcoran et al. | |
| 6,669,708 B1 | 12/2003 | Nissenbaum et al. | |
| 6,669,713 B2 | 12/2003 | Adams | |
| 6,682,536 B2 | 1/2004 | Vardi et al. | |
| 6,736,828 B1 | 5/2004 | Adams et al. | |
| 6,746,472 B2 | 6/2004 | Frazier et al. | |
| 6,746,489 B2 | 6/2004 | Dua et al. | |
| 6,749,621 B2 | 6/2004 | Pantages et al. | |
| 6,773,440 B2 | 8/2004 | Gannoe et al. | |
| 6,835,189 B2 | 12/2004 | Musbach et al. | |
| 6,902,535 B2 | 6/2005 | Eberhart et al. | |
| 6,916,332 B2 | 7/2005 | Adams | |
| 6,921,361 B2 | 7/2005 | Suzuki et al. | |
| 6,921,387 B2 | 7/2005 | Camrud | |
| 6,942,678 B2 | 9/2005 | Bonnette et al. | |
| 6,960,233 B1 | 11/2005 | Berg et al. | |
| 6,966,917 B1 | 11/2005 | Suyker et al. | |
| 6,974,467 B1 | 12/2005 | Gonzales, Jr. | |
| 6,979,290 B2 | 12/2005 | Mourlas et al. | |
| 7,018,401 B1 | 3/2006 | Hyodoh et al. | |
| 7,056,325 B1 | 6/2006 | Makower et al. | |
| 7,077,850 B2 | 7/2006 | Kortenbach | |
| 7,131,948 B2 | 11/2006 | Yock | |
| 7,150,723 B2 | 12/2006 | Meguro et al. | |
| 7,153,314 B2 | 12/2006 | Laufer et al. | |
| 7,156,857 B2 | 1/2007 | Pasricha et al. | |
| 7,169,161 B2 | 1/2007 | Bonnette et al. | |
| 7,182,771 B1 | 2/2007 | Houser et al. | |
| 7,204,842 B2 | 4/2007 | Geitz | |

(56) References Cited

U.S. PATENT DOCUMENTS

| | | | |
|---|---|---|---|
| 7,273,451 B2 | 9/2007 | Sekine et al. | |
| 7,303,531 B2 | 12/2007 | Lee et al. | |
| 7,309,341 B2 | 12/2007 | Ortiz et al. | |
| 7,361,180 B2* | 4/2008 | Saadat et al. | 606/139 |
| 7,377,897 B1 | 5/2008 | Kunkel et al. | |
| 7,390,323 B2 | 6/2008 | Jang | |
| 7,416,554 B2* | 8/2008 | Lam et al. | 606/153 |
| 7,429,264 B2 | 9/2008 | Melkent et al. | |
| 7,534,247 B2 | 5/2009 | Ortiz | |
| 7,591,828 B2 | 9/2009 | Ortiz | |
| 7,731,693 B2 | 6/2010 | Melsheimer | |
| 7,758,565 B2 | 7/2010 | Melsheimer | |
| 7,785,275 B2 | 8/2010 | Melsheimer | |
| 7,845,536 B2 | 12/2010 | Viola et al. | |
| 7,942,890 B2 | 5/2011 | D'Agostino et al. | |
| 7,998,155 B2 | 8/2011 | Manzo | |
| 8,034,063 B2 | 10/2011 | Binmoeller | |
| 8,187,289 B2 | 5/2012 | Tacchino et al. | |
| 2001/0011170 A1 | 8/2001 | Davison et al. | |
| 2002/0111534 A1* | 8/2002 | Suzuki et al. | 600/102 |
| 2002/0183787 A1 | 12/2002 | Wahr et al. | |
| 2002/0188301 A1 | 12/2002 | Dallara et al. | |
| 2003/0014063 A1 | 1/2003 | Houser et al. | |
| 2003/0032975 A1 | 2/2003 | Bonutti | |
| 2003/0040803 A1 | 2/2003 | Rioux et al. | |
| 2003/0045893 A1 | 3/2003 | Ginn | |
| 2003/0050665 A1 | 3/2003 | Ginn | |
| 2003/0069533 A1 | 4/2003 | Kakutani et al. | |
| 2003/0073979 A1 | 4/2003 | Naimark et al. | |
| 2003/0078604 A1 | 4/2003 | Walshe | |
| 2003/0088256 A1 | 5/2003 | Conston et al. | |
| 2003/0093118 A1 | 5/2003 | Ho et al. | |
| 2003/0109900 A1 | 6/2003 | Martinek | |
| 2003/0120292 A1 | 6/2003 | Park et al. | |
| 2003/0163017 A1 | 8/2003 | Tam et al. | |
| 2003/0236536 A1 | 12/2003 | Grigoyants et al. | |
| 2004/0019322 A1 | 1/2004 | Hoffmann | |
| 2004/0034371 A1 | 2/2004 | Lehman et al. | |
| 2004/0049157 A1 | 3/2004 | Plishka et al. | |
| 2004/0073108 A1 | 4/2004 | Saeed et al. | |
| 2004/0122456 A1 | 6/2004 | Saadat et al. | |
| 2004/0199087 A1 | 10/2004 | Swain et al. | |
| 2004/0236346 A1 | 11/2004 | Parker | |
| 2004/0243122 A1 | 12/2004 | Auth et al. | |
| 2004/0249985 A1 | 12/2004 | Mori et al. | |
| 2004/0260332 A1 | 12/2004 | Dubrul et al. | |
| 2005/0033327 A1 | 2/2005 | Gainor et al. | |
| 2005/0043781 A1 | 2/2005 | Foley | |
| 2005/0059890 A1 | 3/2005 | Deal et al. | |
| 2005/0059990 A1 | 3/2005 | Ayala et al. | |
| 2005/0075654 A1* | 4/2005 | Kelleher | 606/151 |
| 2005/0096685 A1 | 5/2005 | Murphy et al. | |
| 2005/0113868 A1 | 5/2005 | Devellian et al. | |
| 2005/0187567 A1 | 8/2005 | Baker et al. | |
| 2005/0222492 A1 | 10/2005 | Adams et al. | |
| 2005/0228413 A1 | 10/2005 | Binmoeller et al. | |
| 2005/0251159 A1* | 11/2005 | Ewers et al. | 606/153 |
| 2005/0251208 A1 | 11/2005 | Elmer et al. | |
| 2005/0277981 A1 | 12/2005 | Maahs et al. | |
| 2006/0015006 A1 | 1/2006 | Laurence et al. | |
| 2006/0062996 A1 | 3/2006 | Chien et al. | |
| 2006/0111672 A1 | 5/2006 | Seward | |
| 2006/0116697 A1 | 6/2006 | Carter et al. | |
| 2006/0142703 A1 | 6/2006 | Carter et al. | |
| 2006/0142790 A1 | 6/2006 | Gertner | |
| 2006/0167482 A1 | 7/2006 | Swain et al. | |
| 2006/0190021 A1 | 8/2006 | Hausman et al. | |
| 2006/0200177 A1 | 9/2006 | Manzo | |
| 2006/0217748 A1 | 9/2006 | Ortiz | |
| 2006/0217762 A1 | 9/2006 | Maahs et al. | |
| 2006/0224183 A1 | 10/2006 | Freudenthal | |
| 2006/0241662 A1 | 10/2006 | Adams et al. | |
| 2006/0259051 A1 | 11/2006 | Nissl | |
| 2006/0259074 A1 | 11/2006 | Kelleher et al. | |
| 2007/0027534 A1 | 2/2007 | Bergheim et al. | |
| 2007/0066863 A1 | 3/2007 | Rafiee et al. | |
| 2007/0112363 A1 | 5/2007 | Adams | |
| 2007/0112383 A1 | 5/2007 | Conlon et al. | |
| 2007/0123840 A1 | 5/2007 | Cox | |
| 2007/0123917 A1 | 5/2007 | Ortiz et al. | |
| 2007/0123934 A1 | 5/2007 | Whisenant et al. | |
| 2007/0135825 A1 | 6/2007 | Binmoeller | |
| 2007/0179426 A1 | 8/2007 | Selden | |
| 2007/0197862 A1 | 8/2007 | Deviere et al. | |
| 2007/0213812 A1 | 9/2007 | Webler et al. | |
| 2007/0260273 A1 | 11/2007 | Cropper et al. | |
| 2008/0065012 A1 | 3/2008 | Hebert et al. | |
| 2008/0071301 A1 | 3/2008 | Matsuura et al. | |
| 2008/0161645 A1 | 7/2008 | Goldwasser et al. | |
| 2008/0167524 A1 | 7/2008 | Goldwasser et al. | |
| 2008/0243151 A1 | 10/2008 | Binmoeller et al. | |
| 2009/0030380 A1 | 1/2009 | Binmoeller | |
| 2009/0177288 A1 | 7/2009 | Wallsten | |
| 2009/0227835 A1 | 9/2009 | Terliuc | |
| 2009/0281379 A1 | 11/2009 | Binmoeller et al. | |
| 2009/0281557 A1 | 11/2009 | Sander et al. | |
| 2010/0105983 A1 | 4/2010 | Oneda et al. | |
| 2010/0130993 A1 | 5/2010 | Paz et al. | |
| 2010/0268029 A1 | 10/2010 | Phan et al. | |
| 2010/0268175 A1 | 10/2010 | Lunsford et al. | |
| 2011/0112622 A1 | 5/2011 | Phan et al. | |
| 2011/0137394 A1 | 6/2011 | Lunsford et al. | |
| 2013/0231689 A1 | 9/2013 | Binmoeller et al. | |
| 2013/0253546 A1 | 9/2013 | Sander et al. | |

FOREIGN PATENT DOCUMENTS

| | | |
|---|---|---|
| EP | 1520526 A1 | 4/2005 |
| EP | 1520532 A2 | 4/2005 |
| EP | 1857135 A2 | 11/2007 |
| GB | 2020557 A | 11/1979 |
| JP | S58-35219 | 3/1983 |
| JP | 62-233168 | 10/1987 |
| JP | H05-137794 A | 6/1993 |
| JP | H05-192407 A | 8/1993 |
| JP | H05-329165 | 12/1993 |
| JP | H05-508563 | 12/1993 |
| JP | H07-096038 | 4/1995 |
| JP | 08-071158 A | 3/1996 |
| JP | 8-504940 | 5/1996 |
| JP | 8-509639 | 10/1996 |
| JP | H08-299455 A | 11/1996 |
| JP | H09-500047 A | 1/1997 |
| JP | H09-504186 A | 4/1997 |
| JP | 10-94543 | 4/1998 |
| JP | 10-155799 A | 6/1998 |
| JP | H11-512318 A | 10/1999 |
| JP | 2000-500045 A | 1/2000 |
| JP | 2000-237303 A | 9/2000 |
| JP | 2001-511658 | 8/2001 |
| JP | 2001-275947 | 10/2001 |
| JP | 2001-517524 A | 10/2001 |
| JP | 2002-119516 | 4/2002 |
| JP | 2002-534208 A | 10/2002 |
| JP | 2003-526448 | 9/2003 |
| JP | 2004-512153 | 4/2004 |
| JP | 2004-216192 | 8/2004 |
| JP | 2005-525865 | 9/2005 |
| JP | 2007514462 | 6/2007 |
| JP | 2008-534029 A | 8/2008 |
| JP | 2009500051 | 1/2009 |
| WO | WO 97/27898 A1 | 8/1997 |
| WO | WO 00/24449 A1 | 5/2000 |
| WO | WO 00/72909 A1 | 12/2000 |
| WO | WO 01/21247 A1 | 3/2001 |
| WO | WO 01/72367 A1 | 10/2001 |
| WO | WO 03/020106 A2 | 3/2003 |
| WO | WO 03/024305 A2 | 3/2003 |
| WO | WO 03/071962 A2 | 9/2003 |
| WO | WO 2005/011463 A2 | 2/2005 |
| WO | WO 2005/096953 A1 | 10/2005 |

(56) References Cited

FOREIGN PATENT DOCUMENTS

| WO | WO 2006/115811 A1 | 11/2006 |
| WO | WO2007115117 A1 | 10/2007 |

OTHER PUBLICATIONS

Fritscher-Ravens, Annette, M.D., et al., Transgastric Gastropexy and Hiatal Hernia Repair for GERD Under EUS Control: A Porcine Model; Gastro Endo; (2004) 59:1, pp. 89-95.

Swain, C. Paul, et al.; Knot Tying at Flexible Endoscopy; Gastro Endo; (1944) 40:6, pp. 722-729.

International Search Report, PCT/US07/04560, mailed Dec. 4, 2007.

Brown et al.; U.S. Appl. No. 13/871,978 entitled "Methods and devices for access across adjacent tissue layers," filed Apr. 26, 2013.

Chopita et al.; Endoscopic gastroenteric anastomosis using magnets; Endoscopy; 37(4); pp. 313-317; Apr. 2005.

Phan et al.; U.S. Appl. No. 13/364,265 entitled "Apparatus and Method for Deploying Stent Across Adjacent Tissue Layers," filed Feb. 1, 2012.

Lepulu et al.; U.S. Appl. No. 13/281,410 entitled "Apparatus and Method for Penetrating and Enlarging Adjacent Tissue Layers," filed Oct. 25, 2011.

Lepulu et al.; U.S. Appl. No. 13/363,297 entitled "Apparatus and Method for Penetrating and Enlarging Adjacent Tissue Layers," filed Jan. 31, 2012.

Binmoeller, Kenneth F.; U.S. Appl. No. 13/709,960 entitled "Method and Apparatus for Performing Needle Guided Interventions," filed Dec. 10, 2012.

Maisin et al.; Patency of endoscopic cystoduodenostomy maintained by a Z stent; Gastrointestinal Endoscopy; 40(6); pp. 765-768; Nov. 1994.

Blum et al.; Endoluminal stent-grafts for infrarenal abdominal aortic aneurysms; NEJM; 336(1); pp. 13-20; Jan. 2, 1996.

Spillner et al.; Initial clainical experiences with endovascular stent-grafts for treatment of infrarenal abdominal aortic aneurysm (in German w/ English Summary); Zentralbl Chir.; 121(9); pp. 727-733; 1996 (year of pub. sufficiently earlier than effective US filing date and any foreign priority date).

Binmoeller et al.; U.S. Appl. No. 14/186,994 entitled "Devices and methods for forming an anastomosis," filed Feb. 21, 2014.

\* cited by examiner

METHODS AND DEVICES FOR ENDOSONOGRAPHY-GUIDED FUNDOPLEXY

CLAIM OF PRIORITY

This application claims priority under 35 U.S.C. §119(e) to U.S. Provisional Application No. 60/688,837, filed Jun. 9, 2005, the entire contents of which are hereby expressly incorporated by reference.

BACKGROUND

1. Field of the Invention

The present invention relates to a tissue securement system, device and method for endoscopy or endosonography-guided transluminal interventions whereby a ligation or anchor is placed and secured into soft tissue.

2. Background of the Invention

Gastroesophageal reflux disease (GERD) is a chronic condition caused by the failure of the anti-reflux barrier located at the gastroesophageal junction to keep the contents of the stomach from refluxing back into the esophagus.

Surgical fundoplication is the gold standard for anatomic correction of the cardia in patients with GERD. However this procedure can have a high incidence of postoperative complications and extended recovery times. Therefore endoscopic methods for enhancing the lower esophageal sphincter have been developed as an alternative to surgery. Endoscopic treatments of GERD target the esophageal and gastric wall in the region of the lower esophageal sphincter. Methods including suture plication, radiofrequency energy ablation, and implant insertion are employed to prevent reflux by mechanisms that include the creation of a mechanical barrier by narrowing the lumen, altering the esophago-gastric angle (angle of His or "flap valve"), and altering the lower esophageal sphincter to enhance its function or decrease transient lower esophageal sphincter relaxations. The endoscopic methods can be performed entirely through the endoscope placed transorally, avoiding any abdominal incisions.

Endoscopic treatment is often limited because the operator can only visualize the mucosal lining of the gastrointestinal wall that is located directly in front of the endoscope. Structures deep within the wall, and outside the wall, cannot be seen. The ability to visualize these structures may influence the proper placement of a treatment apparatus and may expand the therapeutic strategies. For example placement of a suture or ligating element through the esophageal and fundal walls that also includes placement through the diaphragmatic crura may be useful. The use of endoscopic ultrasonography may address this limitation. In this procedure a combination endoscope and ultrasound instrument called an echoendoscope is utilized. From the distal esophagus, pertinent structures visualized with the echoendoscope include the lower esophageal sphincter (LES) within the wall, the crural diaphragm, and the fundus of the stomach. The diaphragmatic crura are typically seen interposed between the distal esophageal wall and the fundus of the stomach. One aspect of this invention utilizes the visualization capabilities of ultrasound endoscopy to permit a novel device and method for treating GERD.

BRIEF SUMMARY OF THE INVENTION

Accordingly, an objective of this invention is to provide a method to reduce gastroesophageal reflux by endosonography-guided intervention. Specifically, endosonography is used to insert a ligation element through the esophageal wall, through the diaphragmatic crus and into the fundus of the stomach. This ligation element placed from the esophagus and around the angle of His may create a barrier to gastroesophageal reflux.

The present invention is directed to a device, system and method that, as embodied and broadly described herein, includes an implantable ligation element for fastening layers of tissue together. The ligation element has proximal and distal ends and is suitable for insertion through the esophageal wall, the crura and into the fundus of the stomach. The distal end of the ligation element can be brought from the fundus, around the gastro-esophageal flap valve and secured to the proximal end of the ligation element in the esophagus. This ligating element forms a loop that can be used to draw the tissues described together.

In a further aspect of the invention, a system for fastening tissue is provided. The system includes a tissue securement apparatus that can be initially positioned in the esophagus using an echoendoscope. The securement apparatus is comprised of a hollow needle with a detachable needle tip. A connecting element is positioned inside the needle and attached to the needle tip. When an inner stylet is advanced, the needle tip separates from the needle body and the needle tip with a portion of the connecting element moves apart from the needle body to reside in the fundus of the stomach.

In another aspect of the invention, the system for fastening tissue also includes a ligating element that can be attached to the proximal end of the connecting element once the hollow needle is removed. The ligating element may utilize a dilating element positioned at its distal end that is sized to dilate a tissue tunnel so that the ligating element may be drawn more easily through the tissue structures.

In still another aspect of the invention, the system may also utilize an endoscopically guided grasper to grasp the distal end of a connecting element and pull the ligating element across the esophageal wall and into the stomach. The system may also utilize a securement element that is configured to engage the proximal and distal ends of the ligating element together. This may prevent the ligating element loop from loosening.

In yet another aspect, the present invention includes a method of treating gastroesophageal reflux disease. In the method, a ligating element having a proximal end and a distal end is passed transorally through the esophagus to a position near the junction between the esophagus and the stomach. The distal end of the ligating element is placed through the wall of the esophagus, through a portion of the diaphragmatic crura and into the gastric fundus using ultrasonic guidance. The distal end of the ligating element is grasped in the fundus, wrapped around the gastro-esophageal flap valve and secured to the proximal end of the ligation element in the esophagus.

All of these embodiments are intended to be within the scope of the present invention herein disclosed. These and other embodiments of the present invention will become readily apparent to those skilled in the art from the following detailed description of he preferred embodiments having reference to the attached figures. The invention is not limited to any particular preferred embodiment(s) disclosed.

DETAILED DESCRIPTION OF THE INVENTION

The system and method described herein may offer improvements over the techniques currently utilized to perform endoscopic procedures. This tissue securement system has several embodiments that are intended to work together to create a novel device and method for the treatment of GERD. However these embodiments also function independently and some of the embodiments of this system may be removed and the system may still achieve its desired function. Alternatively several of these embodiments may be useful as stand alone devices. The principle elements of this system are; an echoendoscope, a delivery needle, a stylet, a needle tip, a connecting element, a ligating element and securement elements.

Figure 1:
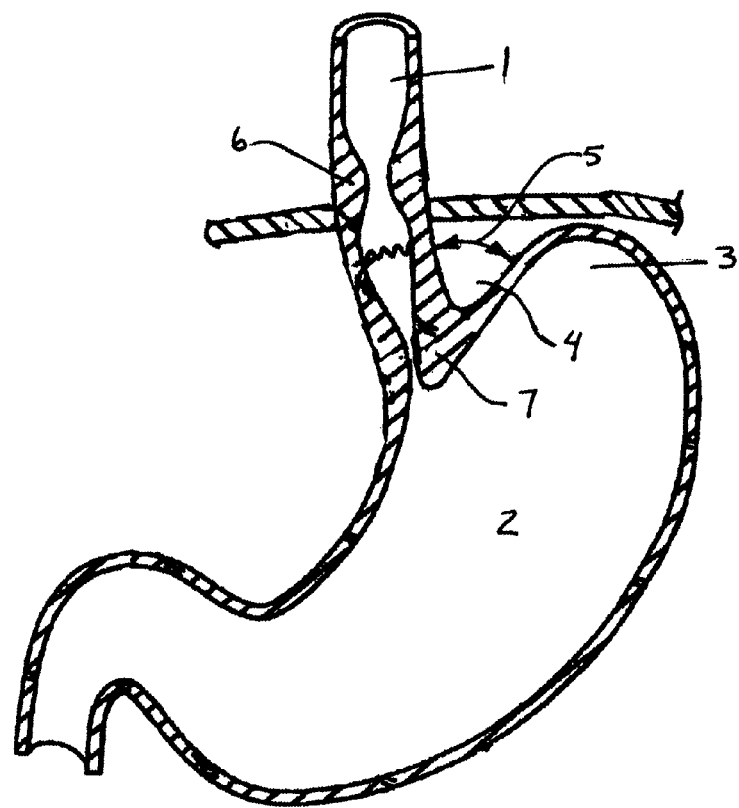
FIG. 1 is a cross sectional view of the esophageal-gastrointestinal tract.

FIG. 1 is a cross sectional view of the esophageal-gastrointestinal tract shown from the esophagus 1 to the stomach 2. The fundus 3 forms the superior portion of the stomach 2. The esophagus 1 enters the stomach 2 at a point below the fundus 3 forming the cardiac notch 4 and an acute angle with respect to the fundus 3 known as the Angle of His 5. The lower esophageal sphincter (LES) 6 is an important primary sphincter that controls the movement of fluids and food into the stomach. The gastro-esophageal flap valve 7 includes a moveable portion and a more stationary portion. The moveable portion is a moveable flap that is formed at the junction of the esophagus 1 and the stomach 2. This flap is approximately 4-5 cm long and is partially held against the opposing wall of the stomach 2 by the internal pressures of the stomach. The esophageal tract is primarily controlled by the LES 6 and the gastro-esophageal flap valve 7. When either the LES 6 or the gastro-esophageal flap valve 7 does not close properly the condition known as Gastroesophageal Reflux Disease (GERD) can occur. It is the intent of this invention to provide a treatment method for GERD by supporting the LES 6 and the gastro-esophageal flap valve 7.

Figure 2:
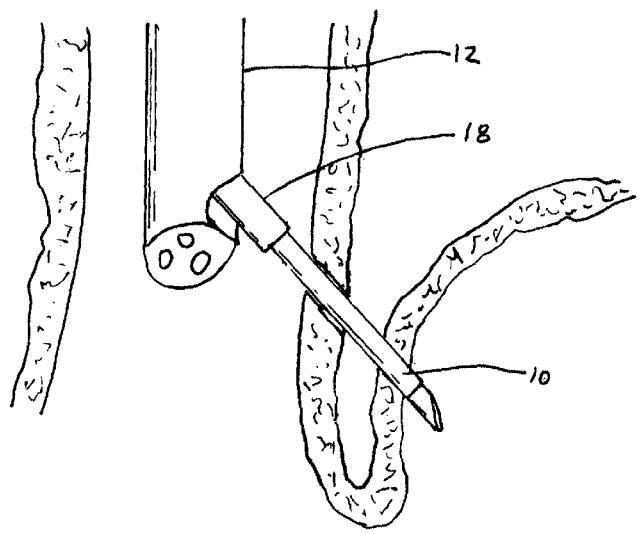
FIG. 2 is a view of the esophagus and stomach showing an echoendoscope placed in the distal portion of the esophagus.
Figure 3:
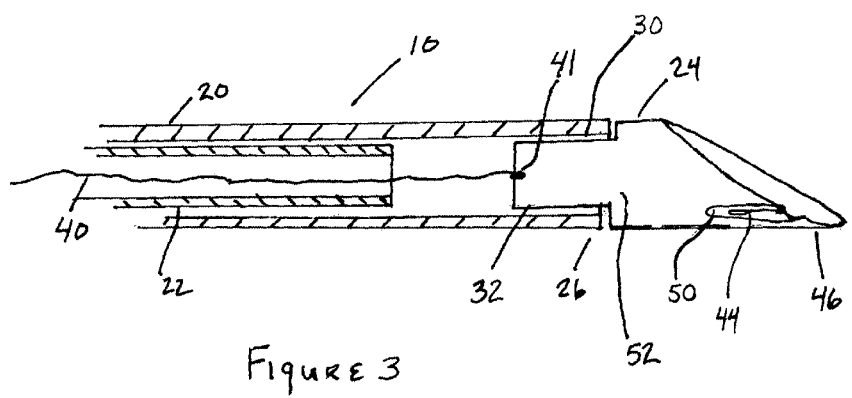
FIG. 3 is a section view of a needle having a detachable needle tip.

A first component of the tissue securement system, the delivery needle 10, is shown in FIGS. 2 and 3 and is designed to be inserted through the instrumentation channel of an endoscope or preferably an echoendoscope 12. The delivery needle 10 can be manually advanced and retracted. The proximal end of the delivery needle may include a handle (not shown) which can be secured to the inlet port of the instrumentation channel by a luer lock mechanism. The delivery needle 10 can be housed in a protective outer sheath 18 which serves to protect the instrumentation channel of an endoscope or echoendoscope from damage from the sharp needle tip and to provide support as the delivery needle 10 is advanced. The outer sheath 18 can be manually advanced to cover the length of the delivery needle 10.

In one embodiment shown in FIG. 3, the delivery needle 10 consists of a needle body 20 which is constructed from a hollow tube and utilizes a hollow stylet 22 located coaxially inside. The delivery needle 10 is sized to fit through the working channel of an echoendoscope although this system may function equally well with larger diametric requirements. The size of the delivery needle 10 is preferably 18 to 26 gauge. More preferably the size is 19 to 23 gauge. A needle tip 24 is located near the distal end 26 of the needle body and is detachably coupled to the needle body 20. The needle body 20 has an inner diameter 30 that provides support to the needle tip 24 during insertion. The needle tip 24 has a mating retention boss 32 located on the proximal end of the needle tip that is formed so that the needle tip 24 fits snugly inside the inner diameter 30 of the needle body 20. Although a peg and hole arrangement is depicted in the drawings, various other features such as a tongue and groove, a bayonet and slot or other common mechanical stabilizing features could easily function with the same intended result; to hold and support the needle tip 24 in position at the end portion of the needle body 20 until the delivery needle is deployed as described later.

A connecting element 40 is connected to the needle tip 24 at point 41 and the connecting element 40 extends through the hollow pusher stylet 22 to the proximal end of the needle where it can be manipulated by the operator outside the patient's body. Upon advancement of the delivery needle 10 into soft tissue, the operator places tension on the connecting element 40 which firmly seats the needle tip 24 in the needle body 20. This facilitates the introduction of the needle body 20 and needle tip 24 through tissue and into a targeted delivery site. Once at the delivery site, the tension can be released. The connecting element 40 is preferably a suture, thread, plastic filament or wire. The pusher stylet 22 extends along the length of the needle body 20 to the proximal end of the needle tip located at the retention boss 32.

Figure 4:
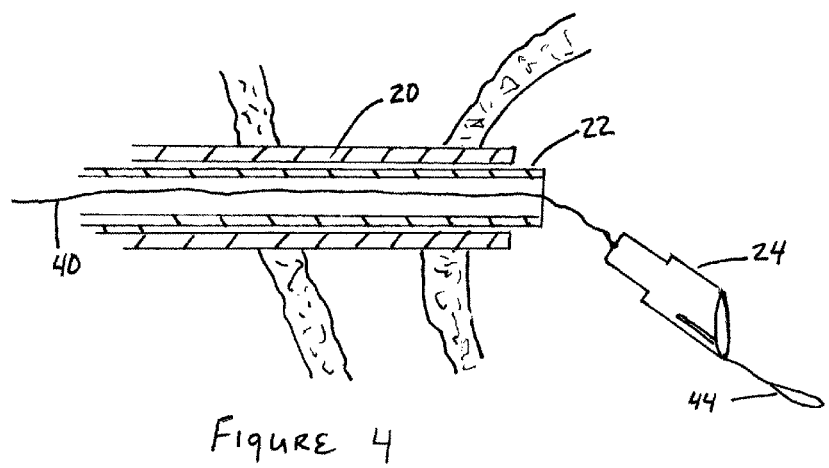
FIG. 4 is a view similar to FIG. 2 showing the needle tip detached from the needle body after placement through a tissue wall.

Once the delivery needle 10 is advanced to a point where the needle tip 24 is at the delivery site, the stylet 22 can be used to deploy the needle tip 24 and connecting element 40. As shown in FIG. 4, when the stylet 22 is advanced the needle tip 24 separates from the needle body 20 and the needle tip 24 and the attached connecting element 40 are delivered to the delivery site. The stylet 22 is next withdrawn into the needle body 20 and the delivery needle 10 can be withdrawn into the protective sheath 18 inside the working channel of an endoscope or echoendoscope. The echoendoscope along with the delivery needle 10 is then withdrawn leaving behind the needle tip 24 with the connecting element 40 extending out through the patient's mouth. The needle tip 24 helps prevent inadvertently pulling out the connecting element 40 from the soft tissue as the echoendoscope 12 and the delivery needle 10 are withdrawn. The connecting element 40 can be attached to the proximal end of the needle tip at 41 or can be connected to a center portion of the tip so that the tip swivels away from the connecting element 40 further preventing inadvertent pullout of the connecting element 40.

The needle tip 24 may utilize a retrieval loop 44 attached near its apex 46 as illustrated in FIGS. 3 and 4. The retrieval loop 44 is a small piece of string or wire that is collapsed along the side of the needle tip 24 while the needle tip 24 is inside the protective sheath 18. The retrieval loop 44 expands once the needle tip 24 and connecting element 40 are deployed as shown in FIG. 4. The retrieval loop 44 may be positioned inside a groove 50 that is formed or cut into the side wall 52 of the needle tip 24. The retrieval loop 44 may be important to guide the needle tip 24 into the working lumen of a gastroscope as the needle tip 24 and connecting element 40 are retrieved as part of the method of this application.

The delivery needle 10 has several potential advantages over other delivery systems that deliver T-tags, plugs or anchors. First, the working channel of a standard echoendoscope has a small diameter in the range of 2.8 mm. This small size limits the size of the needle and T-tag that can be delivered through the working channel. A T-tag may be preloaded inside the hollow core of a needle, but this requires that the T-tag be very small for the procedure. T-tags of this size are difficult to handle by the physician and may be less effective. An alternative to placing the T-tag within a needle requires multiple instrument exchanges whereby first a needle is delivered to the intended site, a guidewire is inserted through the needle lumen, the needle coaxially exchanged for a sheath over the guidewire and the guidewire removed so that a T-tag can be delivered with a pushing stylet. The delivery needle 10 described in this application facilitates a simple delivery of a 19-23 gauge needle tip that acts like a T-tag. This delivery needle can save the operator time and permit delivery of an anchor with a single instrument.

The system so far described is designed to deliver a connecting element 40 and needle tip 24 through soft tissue to an intended delivery site. More preferably this system is designed to deliver the connecting element 40 and the needle tip 24 through the esophageal and stomach wall for the treatment of GERD. In this position, the connecting element 40 can be used to pull another component of the system, a ligating element 60, through soft tissue.

Figure 5:
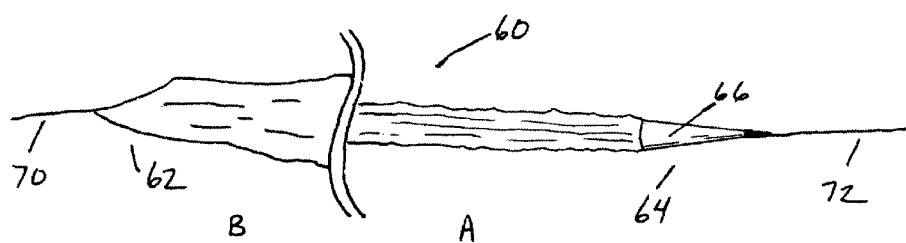
FIG. 5 is a view of a ligating element with an attached dilating element.

The ligating element 60 as shown in FIG. 5 is a length of material that is suitable for long term contact with patient tissue, and is used to tie together layers of soft tissue. It may be a suture, a tie, a thread, a band, a web, a strap, a belt, an elongated piece of mesh, a wire, or a Teflon patch. It may be a single filament or may be folded or coiled up for delivery as illustrated in side "A" of FIG. 5 and then be deployed in an unfolded or uncoiled configuration as illustrated in side "B" of FIG. 5 once in position. It should have enough bulk to reduce the potential for pulling out of soft tissue when force is applied to the ligating element 60. The ligating element 60 has a proximal end 62 and a distal end 64. The distal end 64 of the ligating element 60 can be connected to the proximal end of the connecting element 40 outside the patient's body. The distal end 64 of the ligating element may have a dilating element 66 that is intended to dilate and widen the initial channel through tissue formed by the connecting element 40. The dilating element 66 is a tapered element or bougie that has a diameter similar to the connecting element 40 at its distal end and a diameter similar to the ligating element 60 at its proximal end. It is formed or attached coaxially to the ligating element 60. As the ligating element 60 is drawn into tissue, the dilating element 66 expands the lumen so that the ligating element 60, which may have a larger profile, can transverse the lumen without high forces or causing clinically unacceptable tissue trauma.

Figure 6A:
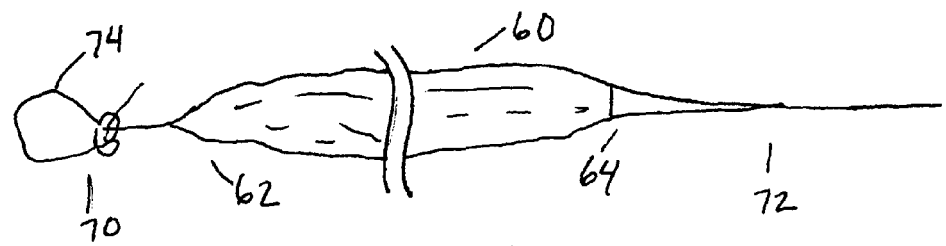
FIG. 6a is a view of a ligating element including one embodiment of a securement element.
Figure 6B:
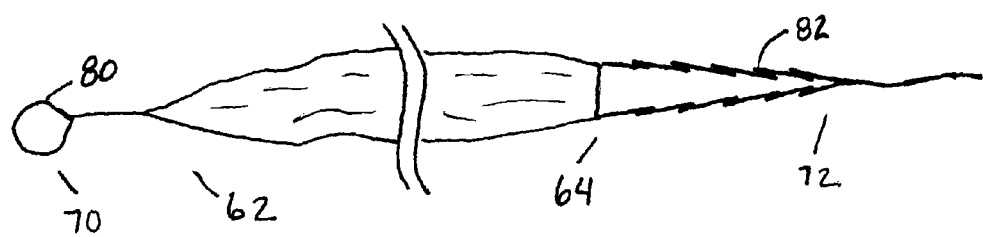
FIG. 6b is a view of a ligating element showing an alternative embodiment of a securement element.

The proximal end 62 and distal end 64 of the ligating element 60 may have securement elements 70 and 72 respectively as illustrated in FIGS. 6a and 6b. The securement elements 70 and 72 are designed to connect both ends of the ligation element 60 together so that the ligation element 60 forms a loop. The securement elements 70 and 72 may incorporate an additional feature which will permit one way slippage so that the diameter of the loop formed can be reduced but not increased. However the ligating element 60 may function equally as well without any securement elements incorporated into the ligating element 60. By example a simple crimping ferrule or wire clip may be utilized with similar results. The securement elements 70 and 72 function similarly to a string loop secured with a slip knot that can be pulled at one end and the loop diameter reduced. As shown in FIG. 6a, the securement element 70 is a suture loop 74 attached to the proximal end of the ligating element 60 formed using a slip knot. The loop 74 is large enough so that a gastroscope can be introduced through the loop. As the distal end 64 of the ligating element is brought through the loop 74, the loop reduces and secures the ligating element 60 in position.

Another embodiment of the securement element 70, shown in FIG. 6b, has a pre formed loop 80 attached to the proximal end 62 of the ligating element 60. The loop 80 is large enough so that a gastroscope can be introduced through the loop 80. The dilating element 66 located near the distal end 64 of the ligating element 60 has a series of grooves 82 that are formed or cut in the side of the tapered dilating element 66. As the dilating element 66 is brought through the loop 80, the series of grooves 82 contact the pre formed loop 80 and the loop 80 successively moves into the recesses of the grooves. This prevents the dilating element 66 from pulling out of the loop 80 but the ligating element 60 can be successively tightened as the dilating element 66 is drawn into the loop 80. Many other types of securement elements such as a rack and pinion, mechanical ratchet are possible and the examples illustrated here are not meant to be limiting. In fact many other suture retention apparatus are equally feasible as known to those in the art.

Methods of treating GERD are discussed with reference to FIGS. 1-8. Although the invention is described in connection with the structure shown in these figures, and in connection with treating GERD, it should be understood that the system in its broadest sense is not so limited.

Figure 7:
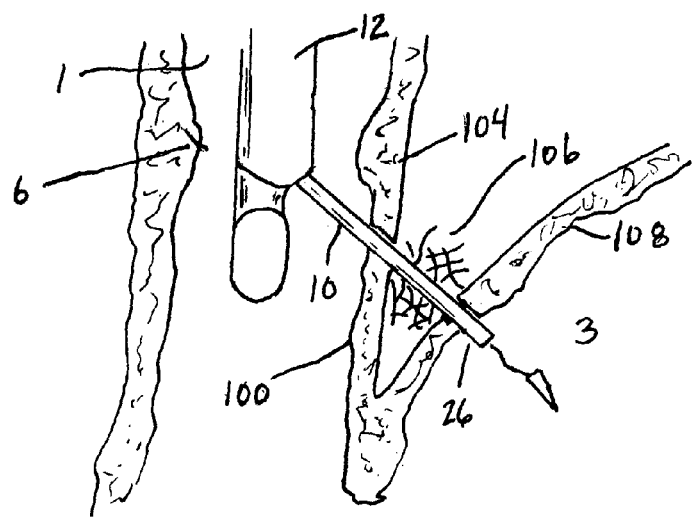
FIG. 7 is a view showing a lower esophageal wall with a delivery needle inserted into the fundus from the esophagus.

As shown in FIG. 7, an echoendoscope 12 is positioned through the patient's esophagus 1 to a position near the lower esophageal sphincter (LES) 6. Although an endoscope 12 may be used an echoendoscope is preferred so that structures and hollow spaces that are positioned behind tissue walls can be visualized. When the echoendoscope 12 is properly positioned, the working channel is directed toward the inner wall of the esophagus 100 and the delivery needle 10 is advanced. The delivery needle 10 pierces the esophageal wall 100 and is then directed through the diaphragmatic crura 106 under ultrasonic guidance and through the wall of the stomach 108 and into fundus 3. It is important that the delivery needle 10 transverse the diaphragmatic crura 106 because is thought that this is a stable structure that will anchor the system as opposed to anchoring to soft tissue alone. Once the distal end 26 of the delivery needle is positioned in the fundus 3, the stylet 22 is advanced to separate the needle tip 24 from the needle body 20. The needle tip 24 with the attached connecting element 40 is deposited in the fundus 3 and the delivery needle 24 is withdrawn. The echoendoscope 12 can be withdrawn leaving behind the connecting element 40 extending from the fundus 3 to the mouth of the patient.

Figure 8:
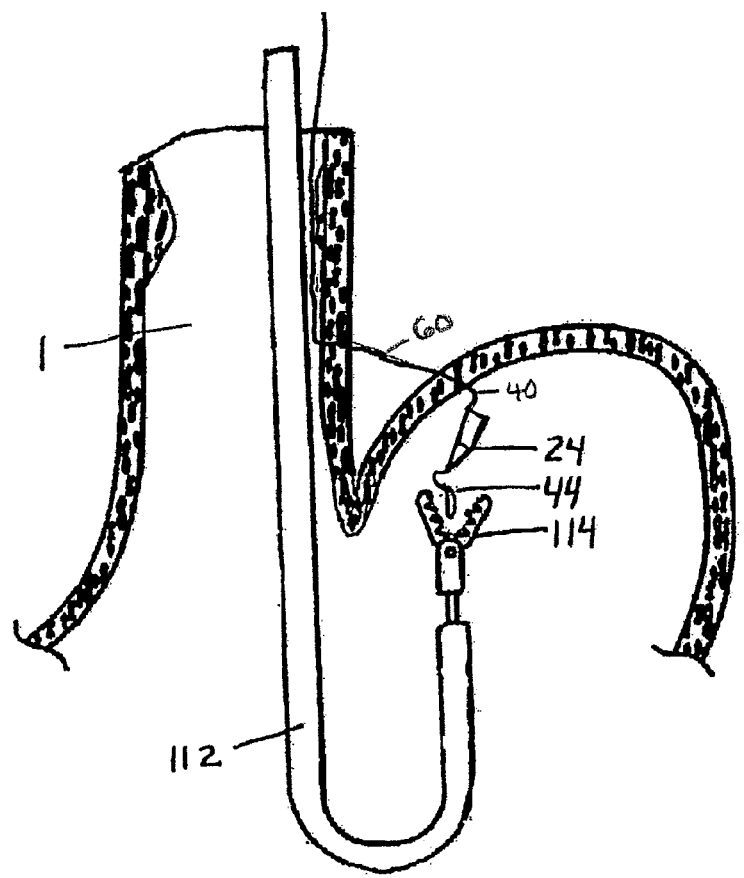
FIG. 8 is a view showing a gastroscope in the stomach with an extended grasper capturing the retrieval loop on the needle tip.
Figure 9:
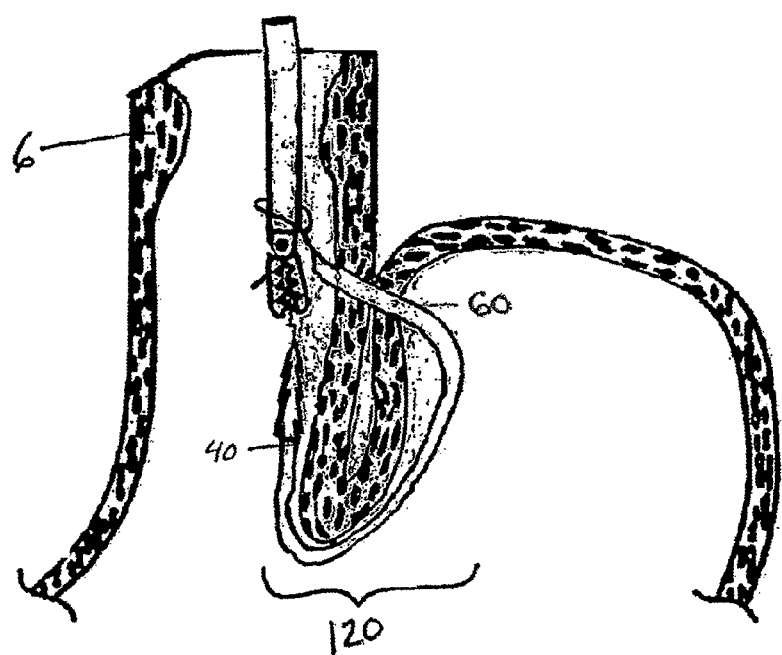
FIG. 9 is a view showing a gastroscope in the lower esophagus with the ligating element forming a loop around the gastro-esophageal flap valve and the stomach drawn up to the lower esophageal wall.

The distal end 64 of the ligating element is attached to the proximal end of the connecting element 40 outside the patient's body. As shown in FIG. 8, a gastroscope 112 is then inserted into the patient's mouth down the esophagus 1 and into the stomach and positioned so that the needle tip 24 and the retrieval loop 44 can be visualized. A grasper 114 is extended from the working channel of the gastroscope 112 and it grabs the retrieval loop 44 of the needle tip 24. The needle tip 24 and connecting element 40 are pulled by the grasper 114 into the working lumen of the gastroscope. The connecting element 40 in turn pulls the ligating element 60 down the esophagus 1 through the esophageal wall 100 and into the fundus 3. The ligating element 60 is drawn near the end of the gastroscope and the gastroscope is withdrawn from the stomach to a position near the LES 6 as shown in FIG. 9. When the securement elements 70 and 72 are brought into close proximity to each other, a loop 120 consisting primarily of the ligating element is formed. This loop 120 formed when the ligating element 60 transverses the esophageal wall 100, the diaphragmatic crura 106, and the fundus 3 of the stomach, around the gastro-esophageal flap valve 7 and back to the esophageal wall 100.

An important feature of the securement elements is that the securement formed between the two ends of the ligating element is slidable so that the diameter of the loop 120 can be reduced to cinch various anatomical features together. By cinching down the loop 120, the fundus 3 of the stomach 2 is drawn into close proximity with the esophageal wall 100. This causes the stomach 2 to be partially wrapped around the esophagus so that esophagus 1 and stomach 2 are positioned in a method similar to a Nissen fundoplication procedure. As the internal pressure of the stomach 2 increases during digestion, the stomach applies a compressive force to the esophagus 1 that tends to reduce the internal luminal diameter of the esophagus. The compressive force reduces the likelihood of the stomach contents being able to pass through the esophagus 1. In other words the lower esophagus functions like a properly functioning lower esophageal sphincter.

This invention has been described and specific examples of the invention have been portrayed. The use of those specifics is not intended to limit the invention in anyway. Additionally, to the extent that there are variations of the invention, which are within the spirit of the disclosure or equivalent to the inventions found in the claims, it is my intent that this patent will cover those variations as well.

What is claimed is:

1. A method for treating gastroesophageal reflux disease comprising:
    inserting a tissue securement apparatus through an esophageal wall, a diaphragmatic crura and a fundal wall of a stomach;
    advancing a connecting element into the stomach;
    joining the proximal end of the connecting element to a ligating element;
    pulling the connecting element to position the ligating element across the esophageal wall, the diaphragmatic crura and the fundal wall of the stomach; and
    fastening the esophageal wall to the fundal wall with the ligating element to capture the diaphragmatic crura between the walls.

2. A method for connecting a first body cavity having an esophageal wall to a stomach having a fundal wall comprising:
    inserting a tissue securement apparatus containing a needle with proximal and distal end portions, through the esophageal and fundal walls, wherein the needle comprises a hollow needle body, a detachable sharpened needle tip, a stylet positioned coaxially inside the needle body, and a connecting element coupled to the needle tip, wherein the tip directly penetrates the walls and a diaphragmatic crura to position the needle tip in the stomach;
    removing the needle body while engaging the stylet against the needle tip to disengage the needle tip from the needle body to leave the needle tip and a portion of the connecting element remaining in the stomach;
    joining a proximal end of the connecting element to a ligating element,
    positioning a grasping forceps inside the stomach and grasping and pulling a distal end of the connecting element to position the ligating element across the esophageal and fundal walls; and
    bringing the ends of the ligating element together to form a loop that draws the esophageal and fundal walls together.

3. The method of claim 2 further comprising delivering the tissue securement apparatus to the first wall using an endoscope or echoendoscope.

4. The method of claim 2 whereby the formed loop traverses around the Angle of His.

5. The advancing step of claim 2 further comprising moving the stylet distally to detach the needle tip from the needle body and position the needle tip with a portion of the connecting element in the stomach.

6. The method of claim 2 further comprising securing the ends of the ligating element with a securement element.

7. A method for repairing a gastroesophageal flap valve comprising:
    positioning a tissue securement apparatus containing a needle with proximal and distal end portions along the esophageal wall wherein the needle comprises a hollow body, a detachable sharpened tip, a stylet positioned coaxially inside the needle body and a connecting element coupled to the needle tip,
    inserting the tissue securement apparatus through the esophageal wall, the diaphragmatic crura and a fundal wall of the stomach, wherein the sharpened needle tip directly penetrates the walls to position the needle tip in the stomach,
    advancing the sylet to push the sharpened needle tip from the needle body so that the needle tip is left in the stomach,
    advancing the connecting element into the stomach,
    withdrawing the needle body,
    joining a proximal end of said connecting element to a ligating element,
    positioning grasping forceps inside the stomach,
    grasping and pulling the connecting element to position the ligating element across the esophageal wall, the diaphragmatic crura and a fundal wall of the stomach, and
    bringing the ends of the ligating element together to form a loop that encircles the gastro-esophageal flap valve and draws the esophageal and fundal walls together.

8. The method of claim 7 further comprising positioning the apparatus with an echoendoscope and using ultrasonic guidance to locate the diaphragmatic crura.

9. The advancing step of claim 7 further comprising moving the stylet distally to detach the needle tip from the needle body and position the needle tip with a portion of the connecting element in the stomach.

10. The method of claim 7 further comprising securing the ends of the ligating element with a securement element.

11. The method of claim 7 further comprising:
    bringing the ends of the ligating element together to form a loop that encircles the Angle of His and draws the esophageal and fundal walls together.

12. The ligating element of claim 7 further comprising an initially folded or coiled configuration suitable for delivery and an unfolded or uncoiled configuration once deployed.

13. The ligating element of claim 7 wherein the ligating element is a suture, tie, thread, band, cord, web, strap, belt, elongated piece of mesh, wire, or a biocompatible patch.

* * * * *